United States Patent
Mandel et al.

(10) Patent No.: US 11,779,760 B2
(45) Date of Patent: Oct. 10, 2023

(54) METHOD AND APPARATUS FOR PORTABLY TREATING MUSCULAR DISCOMFORT

(71) Applicant: Oasis Medical Solutions, LLC, Nevada City, CA (US)

(72) Inventors: William Robert Mandel, Nevada City, CA (US); Margaret Vernon Austin, Nevada City, CA (US)

(73) Assignee: Oasis Medical Solutions, LLC, Nevada City, CA (US)

( * ) Notice: Subject to any disclaimer, the term of this patent is extended or adjusted under 35 U.S.C. 154(b) by 297 days.

(21) Appl. No.: 17/129,498

(22) Filed: Dec. 21, 2020

(65) Prior Publication Data

US 2022/0193409 A1    Jun. 23, 2022

(51) Int. Cl.
*A61N 1/36* (2006.01)
*A61N 1/04* (2006.01)
*A61F 7/00* (2006.01)

(52) U.S. Cl.
CPC .......... *A61N 1/36021* (2013.01); *A61F 7/007* (2013.01); *A61N 1/0452* (2013.01); *A61N 1/0456* (2013.01); *A61N 1/36031* (2017.08); *A61F 2007/0022* (2013.01); *A61F 2007/0071* (2013.01); *A61F 2007/0094* (2013.01)

(58) Field of Classification Search
CPC .............. A61N 1/36021; A61N 1/0452; A61N 1/0456; A61N 1/36031
See application file for complete search history.

(56) References Cited

U.S. PATENT DOCUMENTS

| | | | |
|---|---|---|---|
| 7,468,332 B2 | 12/2008 | Avloni | |
| 8,965,509 B2 | 2/2015 | John | |
| 9,168,375 B2 | 10/2015 | Rahimi et al. | |
| 2006/0195168 A1* | 8/2006 | Dunbar | A61N 1/36021 607/108 |
| 2010/0228304 A1* | 9/2010 | Kriksunov | A61F 7/007 607/46 |
| 2011/0276106 A1 | 11/2011 | Chen | |
| 2017/0128722 A1* | 5/2017 | Perez | A61B 5/021 |

FOREIGN PATENT DOCUMENTS

CN          101939049 B      2/2014

\* cited by examiner

*Primary Examiner* — Amanda K Hulbert
*Assistant Examiner* — Philip C Edwards
(74) *Attorney, Agent, or Firm* — NICHOLSON DE VOS WEBSTER & ELLIOTT LLP

(57) ABSTRACT

Approaches for portably and discreetly treating muscle cramping using one or more of a selectively controllable transcutaneous electrical nerve stimulation (TENS) unit and a heating element comprising resistive fabric. Cramping of the muscle may be detected with a surface electromyography (sEMG) unit. Artificial intelligence techniques may be applied using the sEMG signals and/or user input to identify effective treatment settings.

18 Claims, 13 Drawing Sheets

| RAIL 530 | RAIL 531 | RAIL 532 | RAIL 533 | RAIL 534 | WARM SECN. |
|---|---|---|---|---|---|
| 🔋 | ⏚ | ⏚ | ⏚ | ⏚ | 580 |
| 🔋 | 🔋 | ⏚ | ⏚ | ⏚ | 581 |
| 🔋 | 🔋 | 🔋 | ⏚ | ⏚ | 582 |
| 🔋 | 🔋 | 🔋 | 🔋 | ⏚ | 583 |
| ⏚ | 🔋 | 🔋 | 🔋 | 🔋 | 580 |
| ⏚ | ⏚ | 🔋 | 🔋 | 🔋 | 581 |
| ⏚ | ⏚ | ⏚ | 🔋 | 🔋 | 582 |
| ⏚ | ⏚ | ⏚ | ⏚ | 🔋 | 583 |

*FIG. 7*

| Functon | On | Off | Unit Control | Wi-Fi Control | Auto | Level | Freq. Change | Symbol |
|---|---|---|---|---|---|---|---|---|
| Heating | ✓ | ✓ | ✓ | ✓ | | ✓ | |  |
| TENS | ✓ | ✓ | ✓ | ✓ | | ✓ | ✓ |  |
| sEMG | ✓ | ✓ | | ✓ | ✓ | | |  |
| Bluetooth | ✓ | ✓ | ✓ | ✓ | | | |  |
| Type | | | Button | Screen with buttons and sliders | On Off (see On Control & Wi-Fi Control) | Multiple Button press | Multiple Button press | |
| Indicator | LED | LED | Touch screen | | | Sliders | | |

METHOD AND APPARATUS FOR PORTABLY TREATING MUSCULAR DISCOMFORT

BACKGROUND

From puberty to menopause, women may experience menstrual pain that can sometimes be debilitating. The level and type of pain experienced may vary widely from person to person.

This is also true for other types of muscular pain and discomfort experienced by both men and women due to a variety of different causes.

Approaches for managing and attempting to reduce or alleviate muscular pain and discomfort has taken a range of different forms from medications, to therapies, to devices and more.

BRIEF DESCRIPTION OF THE DRAWINGS

Various embodiments in accordance with the present disclosure will be described with reference to the drawings, in which:

FIG. 7 is a table illustrating example power and ground connections for the rails of the heating element according to some embodiments.

DETAILED DESCRIPTION

In the following description, for the purposes of explanation, numerous specific details are set forth in order to provide a thorough understanding of the embodiments of the invention described below. It will be apparent, however, to one skilled in the art, that embodiments of the invention may be practiced without some of these specific details. In other instances, well-known structures and devices are shown in block diagram form to avoid obscuring the underlying principles of the embodiments of the invention.

For women experiencing menstrual pain, a typical solution may be to curl up with a hot water bottle and wait it out. Most women, however, want to be able to have uninterrupted mobility, and some prefer to avoid the risk of potential side effects that pain relievers and chemical hormone therapy may cause. The same may be true for men and/or women experiencing other types of muscular discomfort.

One alternative is a heating belt, but this type of device may be bulky and obvious to others. Adhesive heating pads may be more discreet, but provide only one type and intensity of treatment, are uncontrolled, and decay over time. A few more recently available devices use adjustable electrical pulses to address the pain and may additionally include acupoint stimulation or massage functions or both. Some example products in this area include two pads, through which the electrical pulses are delivered, to be placed by the user across the area of discomfort.

Described herein are embodiments relating to portable treatment of muscular discomfort, which may include one or more of providing heat and transcutaneous electrical nerve stimulation (TENS). For some embodiments, user input, surface electromyography (sEMG) signals and/or a learning module may be included to provide feedback, refine treatment, track personal data and/or provide data for other uses, for example.

Figure 1:
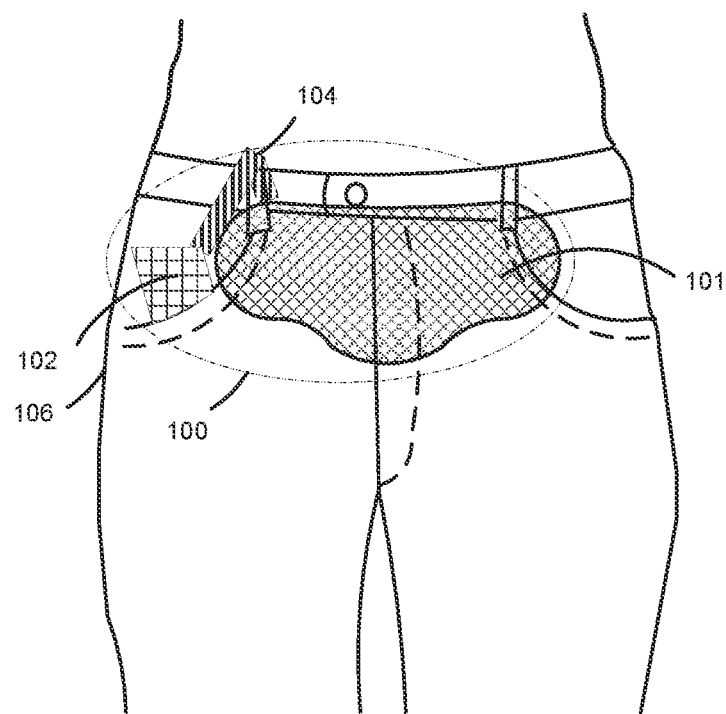
FIG. 1 illustrates the portable treatment apparatus of some embodiments of the invention.

FIG. 1 illustrates the portable treatment apparatus 100 according to some embodiments. The portable treatment apparatus 100 includes a treatment pad 101 to be placed proximate to skin that is proximate to (i.e. covers) a muscular area to be treated, also referred to herein as a treatment area. In other words, the muscular area to be treated, or the treatment area, underlies the treatment pad. For the embodiments illustrated in FIG. 1, the treatment pad 101 of the portable treatment apparatus 100 may be placed on the lower abdomen proximate to the uterus to treat menstrual cramps, and under clothing 106 so it is discreet. The clothing 106 may additionally hold the pad 101 in place. Other muscular organs and muscles in other areas of the body may be treated according to other embodiments using a similar approach. The portable treatment apparatus 100 further includes a treatment control unit 102 electrically coupled to the treatment pad 101 by a connector 104, which may comprise, for example, a ribbon cable or other type of connector. The treatment control unit 102 of some embodiments is small enough to be at least partially concealed in, for example, a jeans pocket or other clothing 106, and may also include ornamental features, a cover, and/or a clip to couple it with clothing 106.

Figure 2:
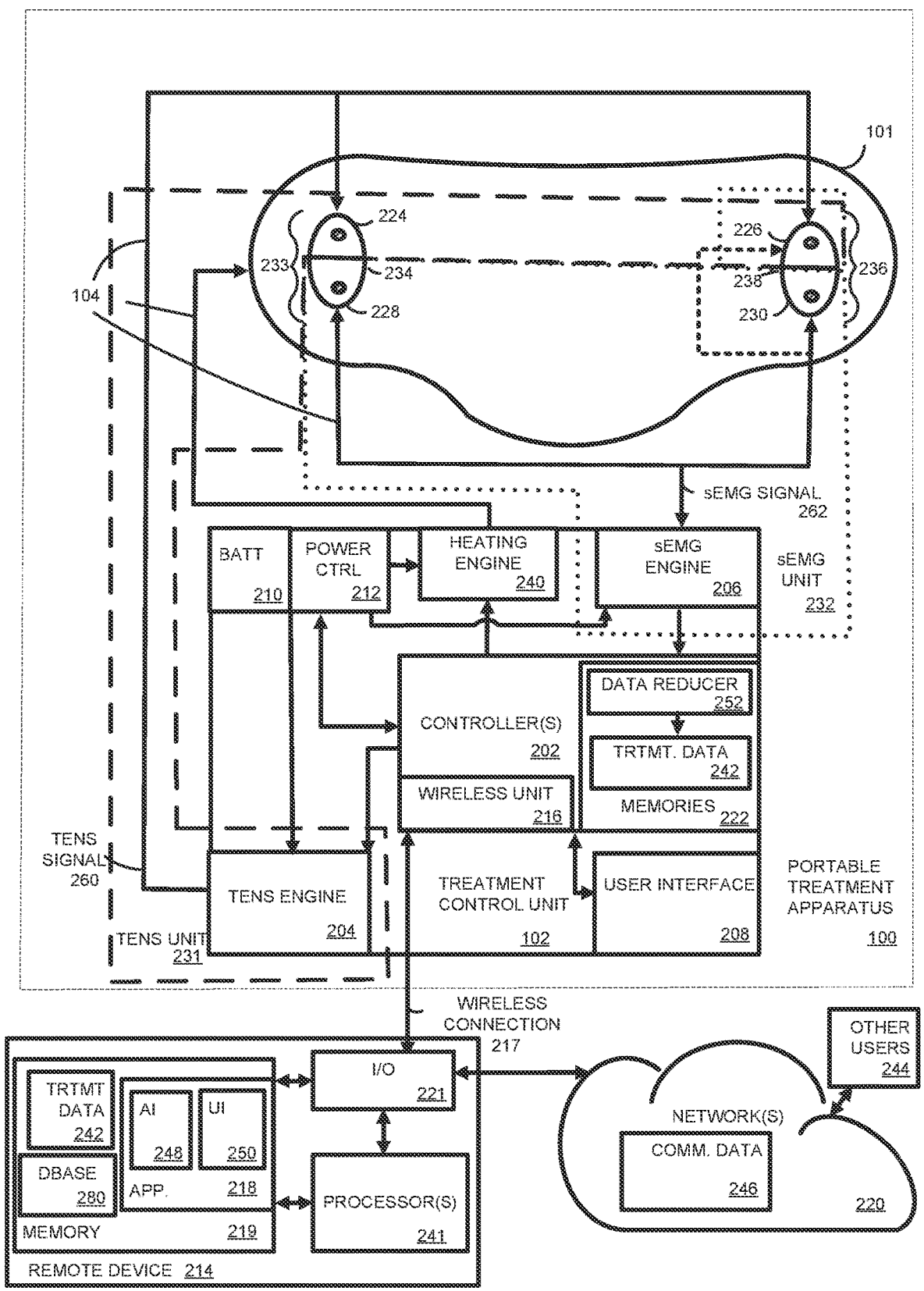
FIG. 2 illustrates the treatment pad and the treatment control unit of some embodiments in further detail.

The treatment control unit 102 is illustrated in more detail in FIG. 2. The treatment control unit 102 includes one or more controllers 202, a transcutaneous electrical nerve stimulation (TENS) engine 204 coupled to the controller(s) 202, a surface electromyography (sEMG) engine 206 coupled to the controller(s) 202, a user interface 208, at least one battery 210 and a battery or power control unit 212 coupled to the battery 210, the controller(s) 202, the TENS engine 204 and the sEMG engine 206.

The controller(s) 202 may comprise one or more microcontrollers, microprocessors, or other processing devices. The controller(s) 202 are coupled to receive user input via user interface 208. For some embodiments, the controller(s)

202 may be further or alternatively coupled to receive user input provided via a remote device 214 that may be accessible via a wireless unit 216 over a wireless connection 217.

The wireless unit 216 may comprise a Bluetooth unit, a Wi-Fi unit, a unit according to another wireless communications protocol or a combination of units that operate according to different wireless communications protocols. The wireless unit 216 may be integrated into the controller(s) 202 as illustrated in FIG. 2 or otherwise coupled to the controller(s) 202.

The remote device 214 may be a cellular, wireless, or handheld device running mobile software and capable of supporting a number of networking and messaging protocols, as well as a desktop, notebook or laptop computer running a standard operating system or other computing device, for example. The remote device 214 includes one or more processors or controllers 241, which may execute instructions stored on the device 214 or that are otherwise accessible by the device 214 such as instructions that are part of a muscle treatment application 218 associated with the portable treatment apparatus 100. The muscle treatment application 218 may be stored locally on the remote device 214 in a memory 219, other storage device, and/or accessible via one or more networks 220 via an input/output unit 221 of the remote device 214.

One or more memories 222 may be included on the controller 202 and/or elsewhere in the treatment control unit 102. A connection between the portable treatment apparatus 100 of some embodiments and networks 220 such as the World Wide Web, or internet, either directly (not shown) or via the remote device 214 allows for additional data storage options, data analysis features, and communication.

The at least one battery 210 of some embodiments includes two 3.7 volt lithium ion batteries. For other embodiments, the at least one battery 210 includes a different number and/or type of battery.

The TENS engine 204 is coupled to deliver TENS signals 260 via positive TENS electrode 224, negative (ground) TENS electrode 226 and connector 104. The sEMG engine 206 is coupled to deliver and detect sEMG signals 262 via positive sEMG electrode 228, negative sEMG electrode 230, for some embodiments as described in more detail below, negative TENS electrode 226, and connector 104. The TENS electrodes 224 and 226 and sEMG electrodes 228 and 230 are coupled to the treatment pad 101 such that they are each electrically coupled to at least a portion of the treatment area through the skin when the treatment pad 101 is placed proximate to the skin covering the treatment area. The TENS engine 204 and TENS electrodes 224 and 226 together are referred to herein as a TENS unit 231. Similarly, the sEMG engine 206 and sEMG electrodes 228 and 230, and for some embodiments, the negative TENS electrode 226, are together referred to herein as an sEMG unit 232. Each of the TENS unit 231 and the sEMG unit 232 may include more electrodes for other embodiments.

For some embodiments, the positive TENS electrode 224 and the positive sEMG electrode 228 are provided on a single electrode pad 233 and are separated by an insulator 234. Similarly, the negative TENS electrode 226 and the negative sEMG electrode 230 may be provided on a single electrode pad 236 and are separated by an insulator 238. The approach of some embodiments for coupling the electrode pads 233 and 236 to the treatment pad 101 is described in more detail below.

For some embodiments, the treatment control unit 102 further includes a heating engine 240 coupled to the controller(s) 202. The heating engine 240 may comprise temperature sensing and heating control circuitry to control heating of the treatment pad 101.

Figure 3:
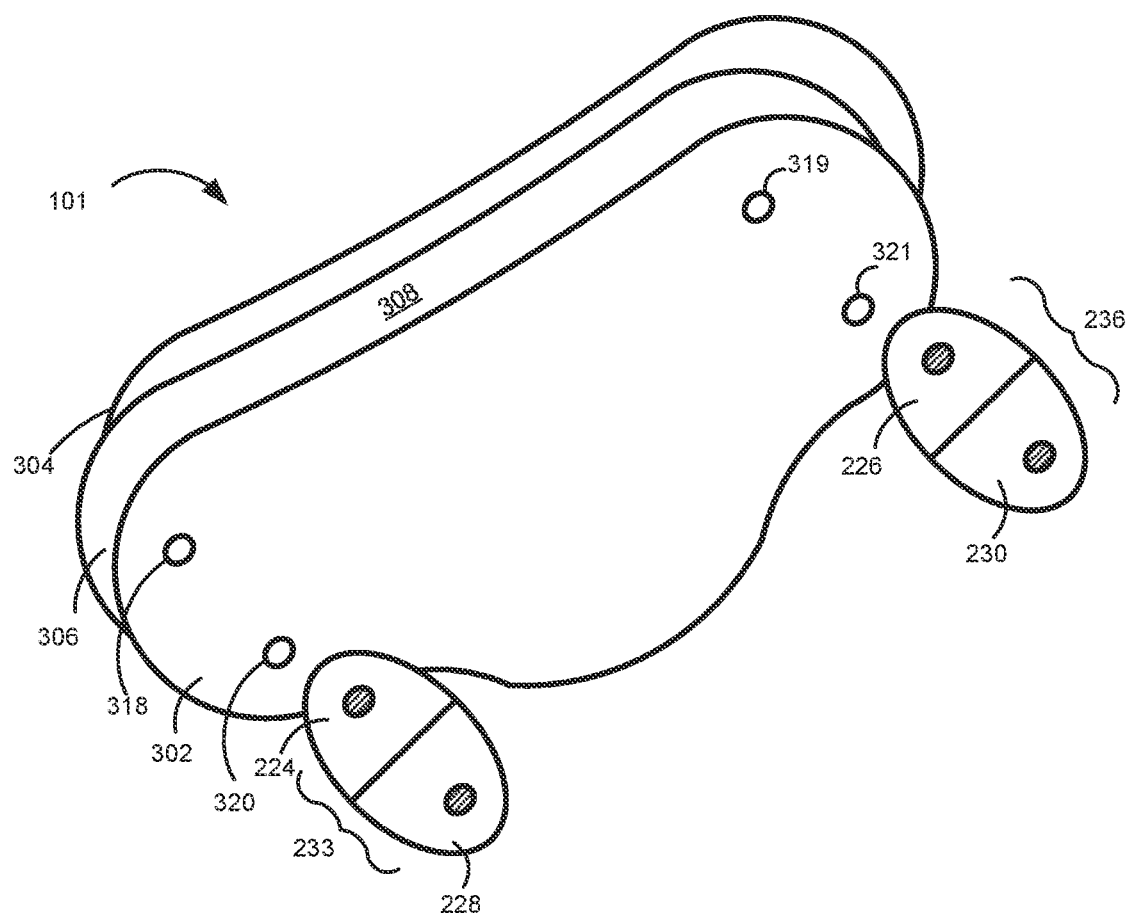
FIG. 3 illustrates example layers of the treatment pad according to some embodiments.

For some such embodiments, referring to FIG. 3, the treatment pad 101 may comprise three layers including first and second outer layers 302 and 304 and a heating element 306 disposed between the first and second outer layers 302 and 304. The first and second outer layers 302 and 304 may be constructed of a fabric that is soft and comfortable to the skin, and that is not conductive. In this manner, the outer layers 302 and 304 substantially electrically insulate the underlying heating element 306 and associated circuitry. For some embodiments, the first and second outer layers 302 and 304 are made of, for example, cotton or polyester blends. Other fabrics and different numbers of layers may be used for other embodiments.

The heating element 306 may comprise a resistive heating fabric 308 such as a conductive polyester and nylon blend, to deliver radiant heating at a relatively low voltage while being thin and lightweight. Using a conductive heating fabric, the heating element 306 may provide more uniform heating as compared with conventional resistive wire heaters. One example of a heating fabric 308 that may be used for the heating element 306 of some embodiments is described in U.S. Pat. No. 7,468,332 to Jamshid Avloni and is currently available under the name Thermionyx Woven Warming Fabric Twill from Eeonyx Corporation. For some embodiments, the heating fabric 308 of the heating element 306 has a sheet resistance of about 36 ohms per square inch. For other embodiments, the heating fabric may be a different type of fabric and/or may have a different sheet resistance, such as a sheet resistance between about 15 and 80 ohms per square inch, although higher or lower sheet resistances are within the scope of various embodiments. For embodiments for which the portable treatment apparatus 100 is used to treat menstrual cramps, the treatment pad 101 may be a rounded triangular shape as illustrated in FIG. 3 with, for example, dimensions at its widest points of about 8 inches by 5 inches. Other shapes and dimensions may be used for other embodiments, including various embodiments directed to treating menstrual cramps.

Figure 4:
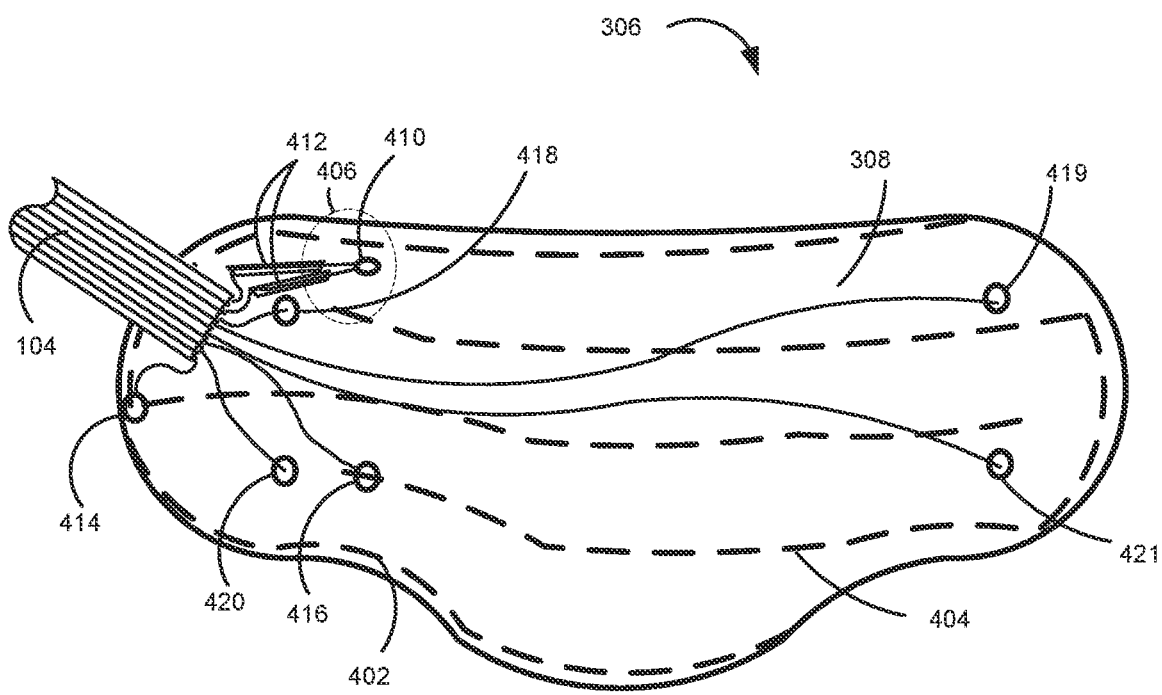
FIG. 4 illustrates an example of a heating element of the treatment pad according to some embodiments.

Referring to FIG. 4, the heating element 306 of some embodiments comprises at least one ground conductive thread 402 and at least one power conductive thread 404. The at least one ground conductive thread 402 and at least one power conductive thread 404 may comprise stainless steel thread having a resistance of about 1.3 ohms ohms/inch. Other types of conductive thread, including conductive threads having a different resistance, may be used for other embodiments. The at least one ground conductive thread 402 and at least one power conductive thread 404 are disposed in a pattern such that they are each reasonably evenly distributed across a desired heating area of the heating element 306 and at a reasonably fixed distance apart from each other across a majority of the desired heating area. This approach provides for more even power (and thus, heat) distribution across the desired heating area and may also enable the heating element 306 to provide more heat at lower voltages.

The conductive threads 402 and 404 of the heating fabric may be sewn onto or otherwise conductively coupled to the heating fabric of the heating element 306. The ground conductive thread(s) 402 and the power conductive thread(s) 404 may be, for example, about 1 inch apart from each other across a majority of the desired heating area. Other separations may be used for other embodiments.

A temperature of the heating element 306 of the treatment pad 101 may be monitored to prevent overheating according to some embodiments. It may be difficult or impractical to monitor every section of the heating element 306, so for some embodiments, in one section 406 of the heating element 306, a portion of each of the ground conductive thread 402 and the power conductive thread 404 are located closer together than the reasonably fixed distance between the ground conductive thread 402 and the power conductive thread 404 in other areas of the heating element 306. Because the conductive threads 402 and 404 are closer together in this section 406, the section 406 will be warmer than other areas of the heating element 306 when power is applied. A temperature sensor 410 may be placed in that area 406 to measure the warmest section of the heating element 306. The temperature sensor 410 may be a negative temperature coefficient (NTC) thermistor, for example. Alternatively, a thermocouple or other type of temperature sensor or temperature measuring device may be used. Where a temperature sensor 410 is used, its connections 412 in this example, may be protected from touching the heating fabric 308 using shrink tubing or another insulating approach. Other approaches for temperature monitoring may be used for other embodiments.

Optionally, a separate apparatus with multiple temperature sensors (not shown) may be used to read various temperature points across the heating element 306 and a digital map may be created. This digital map information may be useful to a manufacturer to identify hot spots to make adjustments to the design for more even heat distribution, for example, or may be provided to the controller(s) 202 and associated software to adjust heating levels for different user settings. This process may also be used to verify that the treatment pad is otherwise correctly constructed and may also be effective in the field.

With continuing reference to FIG. 4, as mentioned above, connector 104 may comprise a ribbon cable to couple various elements of the treatment control unit 102 (FIG. 2) to elements of the treatment pad 101 (FIGS. 1-4) or elements coupled to the treatment pad 101. Ribbon cables may be thinner and less bulky than some other types of connectors while also including redundant wires, which may add strength and may be capable of handling excess current. Other types of conductive connectors may be used for the connector 104 for other embodiments.

The connector 104 may optionally be coupled to the treatment control unit 102 using an approach that provides for easy disconnection if the treatment control unit 102 or treatment pad 101 is pulled on. A strain-relief, non-conducting cord (not shown) that is slightly shorter than the connector 104 may be coupled between the treatment pad 101 and the treatment control unit 102 to serve this purpose and prevent the connector 104 from breaking away. Other approaches for easy disconnection may be used for other embodiments. The connector 104 may also optionally be covered with a fabric wrap, such as a fabric loop with Velcro. Fabric of various colors may come with the unit to customize the look or blend with various outfits.

To power the heating element 306 for some embodiments, connector 104, which is electrically coupled to the treatment control unit 102, is electrically coupled to each of the ground conductive thread(s) 402 and the power conductive thread(s) 404 via separate, electrically isolated wires of the connector 104. For example, the ground conductive thread(s) 402 may be electrically coupled with the connector 104 through a ground conductive grommet 414. Similarly, the power conductive thread(s) 404 may be electrically coupled with the connector 104 through a power conductive grommet 416. For some embodiments, the spacing between the ground conductive grommet 414 and the power conductive grommet 416 is greater than the reasonably fixed distance between the ground conductive thread 402 and the power conductive thread 404 to reduce the risk of the conductive grommet 416 creating a hot spot. For this approach, an end of the respective wire of the ribbon cable connector 104 may be stripped of its insulation and coupled to the respective conductive thread with the respective grommet, which may be crimped, soldered or otherwise conductively coupled to the heating fabric 308. Other approaches for powering the heating element 306 may be used for other embodiments.

To electrically couple the TENS engine 204 (FIG. 2) with the TENS electrodes 224 and 226, for some embodiments, one or more insulated wires of the connector 104 are passed through a TENS positive eyelet 418 and another one or more insulated wires of the connector 104 are passed through a TENS negative eyelet 419. The opposite ends of the wires passed through the TENS positive eyelet 418 and the TENS negative eyelet 419 are conductively coupled to the TENS engine 204. Similarly, to conductively couple the sEMG engine 206 (FIG. 2) with sEMG electrodes 228 and 230, and, for some embodiments, TENS negative electrode, one or more insulated wires of the connector 104 are passed through an sEMG positive eyelet 420, one or more wires of the connector 104 are passed through an sEMG negative eyelet 421, and, for embodiments that additionally couple the TENS negative (ground) electrode to the sEMG engine, one or more additional wires of the connector 104 are passed through the TENS negative eyelet 419. The opposite ends of the wires passed through the sEMG positive eyelet 420, the sEMG negative eyelet 421, and for some embodiments, the one or more additional wires passed through the TENS negative eyelet 419 are conductively coupled to the sEMG engine 206. The TENS and sEMG eyelets 418-421 may be small grommets that may or may not be conductive. The eyelets 418-421 may be coupled with the heating fabric 308 using a similar approach to grommets 416 and 418. In the case of TENS and sEMG eyelets 418-421, however, a portion of the heating fabric inside the respective eyelet is removed to enable the respective wire to pass through the eyelet.

Although low voltage may not produce a dangerous shock to the body, it is still desirable for various embodiments to protect the heating fabric from getting wet. Control and other circuitry in the treatment control unit 102 may be destroyed if the conductive threads 402 and 404 of the heating unit 306 become electrically coupled. The heating element 306 of some embodiments is water-proofed as an additional protection for the unit. This may be done by dissolving silicone in acetone and applying it as a liquid to both sides of the heating element 306 after the conductive threads 402 and 404 and other conductive elements have been coupled with the heating element 306. Other approaches for water-proofing the heating element 306 may be used for other embodiments.

Referring back to FIG. 3, after the insulated wires from the connector 104 are passed through the TENS and sEMG eyelets 418-421, they are each passed through a respective small opening (not shown) in the first outer layer 302 underlying a respective one of multiple electrode attachment receptacles 318-321. The insulation on a portion of each wire that extends through the first outer layer is stripped and the exposed conductive portion of the wire is conductively coupled to the respective one of the electrode attachment receptacles 318-321 such that the conductive portion of the wire is enclosed within the receptacles 318-321 or otherwise does not make contact with underlying conductive areas.

The electrode attachment receptables 318-321 are disposed on a surface of the first outer layer 302 that is not facing the heating element 306.

Snap-on electrode pads 233 and 236 are then coupled with the electrode attachment receptacles 318-321 in a manner that electrically couples positive TENS electrode 224 with the electrode attachment receptacle 318 and negative TENS electrode 226 with the electrode attachment receptacle 319, all of which are electrically coupled with the TENS engine 204 as described above in reference to FIG. 2. Similarly, sEMG positive electrode 228 is electrically coupled with electrode attachment receptacle 320 and sEMG negative electrode 230 is electrically coupled with electrode attachment receptacle 321, all of which are electrically coupled with the sEMG engine 206. Other approaches for coupling the various elements of the TENS and sEMG units 231 and 232 are within the scope of other embodiments.

With continuing reference to FIG. 3, the layers 302, 304 and 306 of the treatment pad 101 may be coupled together for some embodiments by sewing the outer layers 302 and 304 together with outside surfaces facing each other and leaving an opening through which the connector 104 (FIG. 2) can extend. The coupled outer layers 302 and 304 may then be pulled through the opening such that their rough edges are enclosed. The heating element 306 may be sewn on to an outer edge of the outer layer 302, for example, either before or after pulling the layers 302 and 304 through the opening. The connector 104 may be pulled through the opening and coupled with the treatment control unit 102. Other approaches for coupling the various layers may be used for other embodiments.

Figure 5:
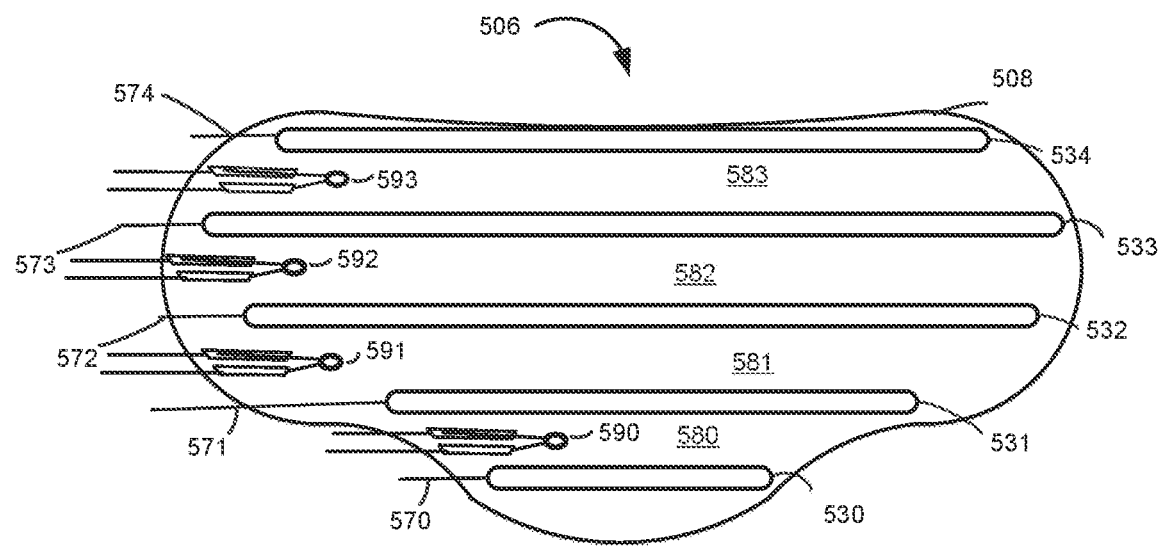
FIG. 5 illustrates an alternative example of a heating element of the treatment pad according to some embodiments.

FIG. 5 illustrates a heating element 506 that may alternatively be used in place of the heating element 306 for some embodiments. Instead of conductive threads as described in reference to FIG. 4, the heating element 506 comprises conductive rails 530-534 conductively coupled to heating fabric 508. The heating fabric 508 may be the same material as the heating fabric 308 for the heating element 306 of FIG. 3, for example. For some embodiments, the rails 530-534 comprise copper foil, but other conductive materials may be used for other embodiments.

Figure 6:
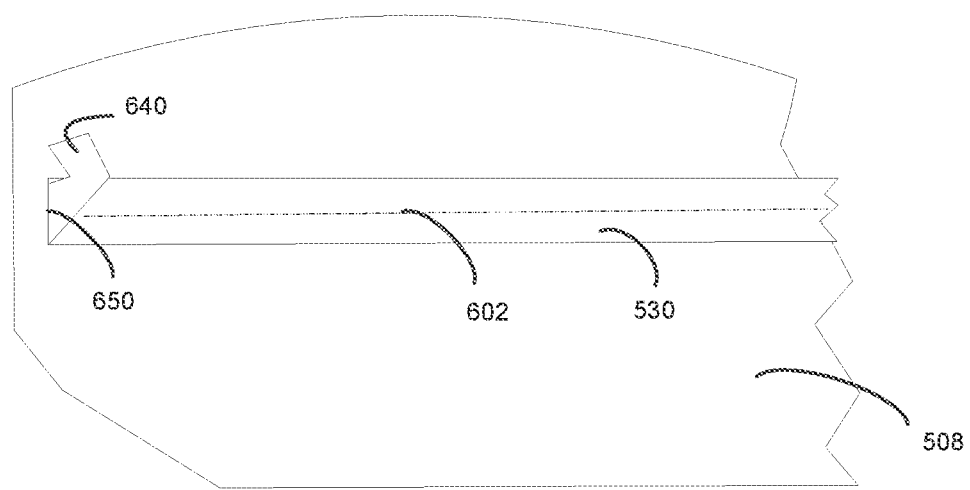
FIG. 6 illustrates a more detailed view of an example rail of some embodiments.

FIG. 6 illustrates a more detailed view of one of the rails 530. The rail 530 is sewn to the heating fabric 508 with a thread 602. The thread 602 may comprise either conductive thread or non-conductive thread. If the copper foil of the rail 530 includes an adhesive backing between the rail 530 and the heating fabric 508, it may be desirable for the thread 602 to comprise a conductive thread to increase conductivity between the rail 530 and the heating fabric 508. If the copper foil of the rail 530 does not include an adhesive or includes an adhesive, but the adhesive is not between the rail 530 and the heating fabric 508, the thread 602 may alternatively comprise a non-conductive thread. A tail 640 of additional copper foil may remain free from the thread 602 such that wires of the connector 104 may be soldered at a solder point 650 or otherwise conductively coupled to the rail 530. Other approaches for coupling the rails 530-534 to the heating fabric 508 may be used for other embodiments.

Referring back to FIG. 5, in operation, each of the rails 530-534 may be selectively coupled to ground or to a power source by the treatment control unit 102 via wires 570-574 of connector 104. More specifically, the controller(s) 102 (FIG. 2), may control the selective coupling of rails 530-534 to a ground rail or a power rail via the heating engine 240 and the power control unit 212. The heating of sections 580-583 of the heating element 506, where each section 580-583 extends substantially across the heating element 506 between the respective adjacent rails, may be controlled, at least in part, based on selectively controlling the power and ground connections to the rails 530-534. For some embodiments, the heating element 506 further comprises temperature sensors 590-593, each of which is coupled to the treatment control unit 102 via connector 104 in a manner similar to the temperature sensor 410 of FIG. 4.

Referring to FIGS. 5 and 7, viewing FIG. 7 by row, for the embodiments described above, if rail 530 is coupled to operate as a power rail and rails 531-534 are all coupled to operate as ground rails, only section 580 produces heat. If rails 530 and 531 are coupled to operate as power rails and rails 532-534 are coupled to operate as ground rails, only section 581 produces heat. If rails 530-532 are coupled to operate as power rails, and rails 533 and 534 are coupled to operate as ground rails, only section 582 produces heat. If rails 530-533 are coupled to operate as power rails and rail 534 is coupled to operate as a ground rail, only section 583 produces heat. If power and ground are interchanged in each of the above examples, the same section produces heat as shown in the last four rows of FIG. 7.

For some embodiments, the treatment control unit 102 selectively couples each of the rails 530-534 to power or ground as described above to heat one section 580-583 of the heating element 506 at a time until the associated temperature sensor 590-593 senses that the respective section 580-583 has reached a desired temperature. The desired temperature may be based, for example, on a heat intensity setting for the heating element 506. In response to the respective section 580-583 reaching the desired temperature, the treatment control unit 102, selectively couples each of the rails 530-534 to power or ground to heat a different section until the associated temperature sensor 590-593 senses that the respective section 580-583 has reached a desired temperature. For this embodiment, this sections 580-583 may be heated one at a time in a cycle during the time that the heating element 506 is controlled by the treatment control unit 102 to provide heat. Using this approach, it may be possible for some embodiments to effectively provide heat via the heating element 506 while limiting the power through the connector 104 and enabling the use of lower voltages for the battery 210 as compared to powering all or multiple sections at the same time. Further, the overall power distribution is limited to each section at any one time and yet maintains the overall distribution of heat across the entire region to be heated for some embodiments. For other embodiments, different heating patterns may be implemented by using different combinations and/or patterns of powering or grounding each of the rails 530-534.

The operation of some embodiments is further described using treatment of menstrual cramps as an illustrative example. It will be appreciated that other types of muscle discomfort may be treated using a similar approach according to some embodiments, with adjustments specific to the type and location of the muscle(s) to be treated. Referring to FIGS. 1 and 2, a user may initiate treatment by placing the treatment pad 101 proximate to the treatment area such that electrode pads 232 and 236 are in contact with skin covering the treatment area. User interface 208 is used to enable and control the various functions of the portable treatment device 100. The user interface 208 may include one or more of button(s), a touch screen, one or more sliders and/or another type of user input. The user interface 208 may also include one or more indicators such as a graphical user interface, one or more light emitting diodes (LEDs) and/or another type of indicator. The user interface 208 is shown in FIG. 2 as being integrated into the treatment control unit 102. For other embodiments, the user interface 208 may be accessible via the remote device 214 through an application such as the muscle treatment application 218, through a web-based interface via the network(s) 220, or may be provided through any combination of the treatment control unit 102, the remote device 214 and the network(s) 220.

Figure 8:
FIG. 8 illustrates example user controls and user interface symbols of some embodiments.
Figure 8:
Figure 8:
Figure 8:

Via the user interface 208, a user may selectively enable and control heating, TENS and/or sEMG functions, described in more detail below, as well as other features and functions such as Bluetooth for some embodiments. An example of one approach to providing user controls is illustrated in FIG. 8. For some embodiments, a single button of the user interface 208 may turn the treatment control unit 102 on and determine a heat setting (e.g. high, medium or low). An LED may blink once to indicate a lowest setting. Subsequent pushes of the button may be used for higher heat settings with an LED blinking a corresponding number of times. Once the highest heat setting is reached, a subsequent press of the button may turn the treatment control unit 102 off and the LED light may gradually fade. A similar approach may be used to control a TENS setting for some embodiments. Other functions may be controlled and indicated as shown in FIG. 8. This is just one of a multitude of options for providing a user interface. Other approaches may be used for other embodiments.

TENS therapy involves the use of low-voltage electric currents (TENS signals) to treat pain or discomfort. The TENS engine 204 is capable of producing TENS signals 260 of different frequencies and/or different intensities (i.e. peak values) in response to user input. TENS electrodes 224 and 226 placed on the body near a treatment site can deliver electricity in the form of the TENS signals 260 from the TENS engine 204 that travel through the underlying skin to and through nerve fibers in the area to be treated. The electric currents delivered by the TENS signals 260 may block pain receptors from receiving messages from associated nerve fibers through the brain.

The heating engine 240 is responsive to the controller 102 to control the heating element 306 (FIG. 3) or 506 (FIG. 5) to provide heat to the treatment area via the treatment pad 101. For some embodiments, the heating engine 240 provides different heating levels or intensities (i.e. heat of different temperatures) in response to user input as described.

The sEMG unit 232 measures muscle tension by detecting a level of electrical activity released by a muscle when it is contracting. The sEMG unit 232 is similar in operation to an electrocardiogram (ECG or EKG) unit, for example, which measures heart muscle activity. sEMG muscle tension measurement typically uses a minimum of 3 electrodes: two for incoming signals and a third for ground. For some embodiments, the sEMG ground is provided by the TENS negative electrode 228. The incoming sEMG signals are received via sEMG electrodes 228 and 230. These incoming signals collectively comprise the sEMG signal 262, which is provided to the sEMG engine 206 and controller 202 where it is processed and converted to digital sEMG data using, for example, one or more analog to digital converters within the controller 202. A peak value of the sEMG signal 262 indicates a strength or intensity of cramping of a muscle to be treated. A time between signal peaks of the sEMG signal 262 further indicates a time between muscle cramps. Using the sEMG unit 232 of some embodiments may allow a user to, for example, understand her menstrual cycle patterns. Data indicating sEMG measurements may be accessible to a user via, for example, the muscle treatment application 218 available on or accessible by the remote device 214. Other options for indicating muscle tension measurements by the sEMG unit 232 may be used for other embodiments.

In the case of menstrual cramps, if the intensity, i.e. peak value of the sEMG signal 262, is increasing from one cramp to the next, it may be an indication that the user has not yet reached the peak of her cramping cycle. If the intensity is decreasing from one cramp to the next, on the other hand, it may be an indication that the user is approaching the end of that particular cycle. Similarly, if the time between cramping cycles, as indicated by the time between sEMG signal 262 peaks, is decreasing, it may be an indication that a menstrual cycle flare is approaching its peak. In contrast, if the time between signal 262 peaks is increasing, it may be an indication that the menstrual cycle flare is on the other side of its peak and approaching an end. A similar feedback process may be useful for other types of muscle cramping. Although everyone's body is unique and different, this measurable feedback process may allow a user to better understand her/his body and how it functions. This process may also allow a user to determine, through experimentation, a frequency and an intensity of the TENS signal 260, level of heating via the heating element 306 (FIG. 3) or 506 (FIG. 5), or combination of both TENS and heat settings that is effective in alleviating pain associated with menstrual cramps or other muscle cramping.

Figure 9:
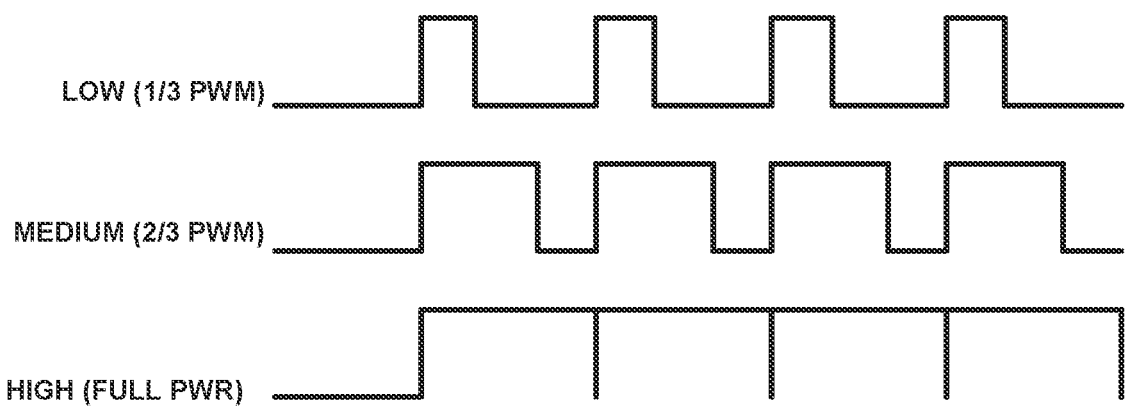
FIG. 9 illustrates example pulse trains at various power levels that control the heating level of the portable treatment apparatus of some embodiments.

For some embodiments, a level of heating provided by the heating engine 240 through the heating element 306 (FIG. 3) or 506 (FIG. 5) is responsive to a power signal from the power control unit 212. This power signal from the power control unit is modulated by the controller 202 in response to input received via user interface 208 or another input source such as the remote device 214. For some embodiments, the heating level may be selectively set to high, medium, or low intensity as previously described. An example of the duty cycles for the power signals to control the heating level is shown in FIG. 9. For other embodiments, the heating level may include a different number and range of settings.

A frequency and intensity of the TENS signal 260 may be controlled by the TENS engine 204 through the TENS electrodes 224 and 226 in response to input received via user interface 208 or another input source such as user input via the remote device 214 or the application 218.

With the above-described features and functions of some embodiments, TENS, heat, or both may be selectively applied at different levels to treat muscle discomfort. Further, the use of sEMG may provide a user with information about muscle cramping cycles and/or the effectiveness of different treatments.

Referring back to FIG. 2, for embodiments including a muscle treatment application 218 stored in a memory 219 and executable by a processor 241 of the remote device 214 or otherwise accessible by a remote device 214 (e.g. via network(s) 220), additional features and functions may be provided. For example, the treatment control unit 102 may be controlled via the remote device 214 as described above. Additionally, sEMG and/or other treatment data 242, such as real-time data from the heating device 306 (FIG. 3) or 506 (FIG. 5), and also historical data stored in the memory 222, the memory 219 or another memory, may be provided to the muscle treatment application 218 on the remote device 214 or over the network(s) 220. This treatment data 242 may include, for example, 1) heat treatment data including a treatment start time, an intensity used, and a treatment end time for heating and/or 2) TENS treatment data including a treatment start time, intensity, frequency and treatment end time for TENS therapy, 3) sEMG data indicating muscle activity before treatment, during treatment and/or in response to one or more of a) intensity settings for heat, b) intensity and/or frequency settings for TENS, c) user input (e.g. effectiveness of treatment, pain level, other personal factors), or any combination or subset of treatment data thereof. Other treatment data may be provided for other embodiments.

The treatment data 242 that is collected may be solely accessible by a user for his or her own purposes. Alternatively, for some embodiments, the muscle treatment application 218 may include an option to join a community or otherwise share the treatment data 242 more broadly with other users 244. For example, treatment data 242 may be optionally provided into a collective anonymous community database 246 and may be useful in identifying more effective interventions or, conversely, reveal options that have not been effective. Options to include other personal data such as age, location, activity level, etc. may also be included for other embodiments to potentially suggest other interventions.

For some embodiments, at least one muscle treatment learning module, such as an artificial intelligence (AI) module 248 (described in more detail in reference to FIG. 10), including machine learning (ML), such as an artificial neural network (ANN), may be used to find effective treatment settings for an individual. For such embodiments, the muscle treatment AI, ML or ANN module(s) may be part of the muscle treatment application 218 stored in the memory 219 and accessible to a user through a user interface 250.

In the case of treating menstrual cramps, each person has individual biological dynamics that influence what works and what does not work for pain relief. Muscle contractions may be monitored by the muscle treatment AI 248 via the sEMG unit 232 for time and intensity while applying different TENS frequencies and/or intensities, and/or different heating levels. The muscle treatment AI 248 may then, for example, be able to identify the best TENS settings and/or heat settings to reduce cramping events.

Figure 10:
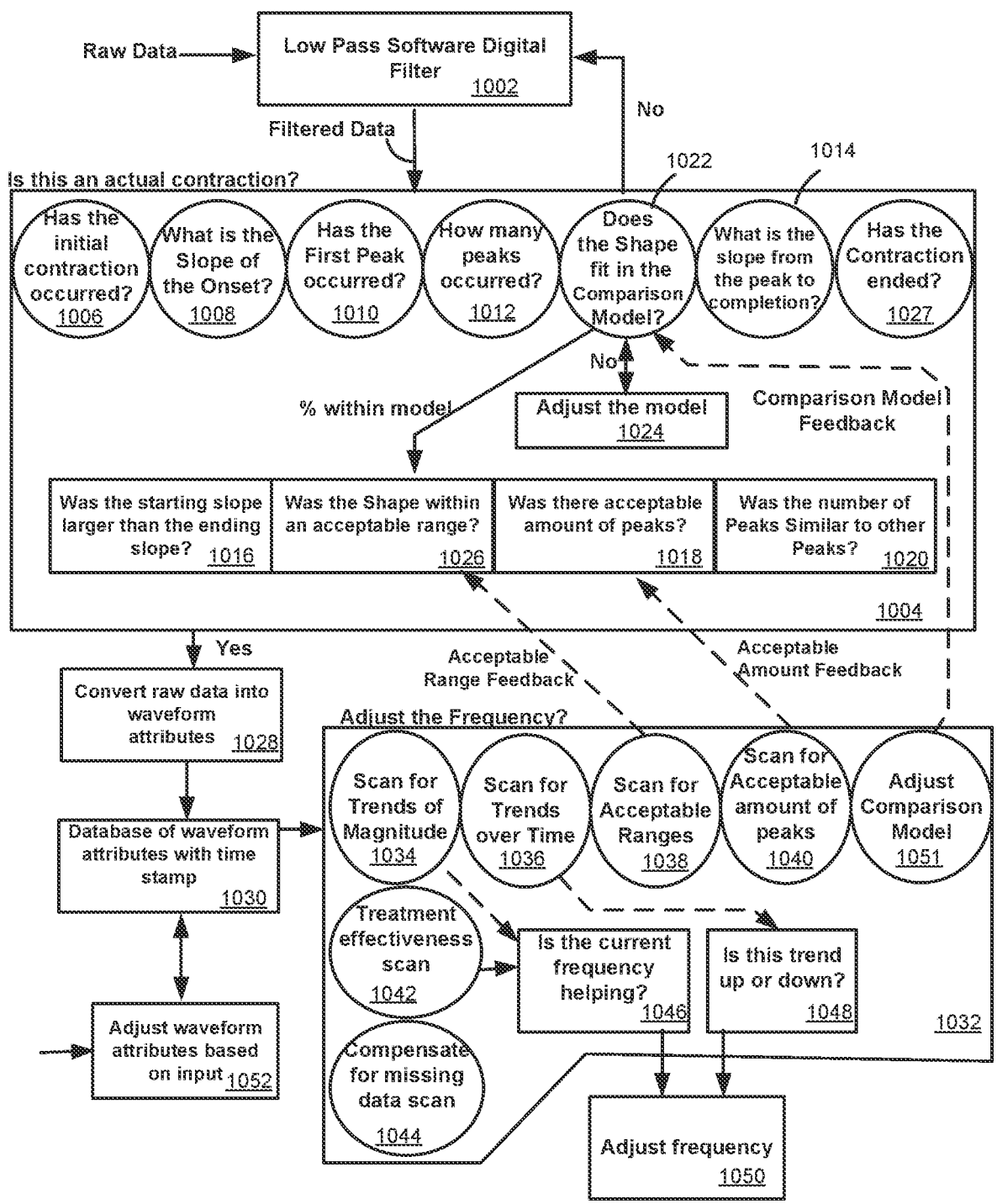
FIG. 10 illustrates an example process of some embodiments that may be used to identify effective settings for the portable treatment apparatus.

Some embodiments of a process that may be used to identify effective settings are described in more detail in reference to FIG. 10. Some or all of the operations (or other processes described herein, or variations, and/or combinations thereof) are performed under the control of one or more computing devices or systems configured with executable instructions and are implemented as code (e.g. executable instructions, one or more computer programs, or one or more applications) executing collectively on one or more processors, by hardware or combinations thereof. The code is stored on a computer-readable storage medium, for example, in the form of a computer program comprising instructions executable by one or more processors. The computer-readable storage medium is non-transitory. In some embodiments, one or more (or all) of the operations are performed by the AI 248, as part of the application 218.

Prior to initiating the process to identify effective settings, one or more comparison models (such as the model of FIG. 11) may be loaded into a database 280 that is accessible by the muscle treatment application 218. For some embodiments, raw data is received at an input such as a low pass software digital filter at block 1002 to produce filtered data. The raw data may be received, for example, from sEMG signals 262 via the sEMG engine 206, user input via user interface 208 or the muscle treatment application 218. The low pass software digital filter may be included as part of the sEMG engine 206 for some embodiments or elsewhere on treatment control unit 102.

At block 1004, it is determined whether the filtered data represents a muscular contraction. Many factors may be considered in this determination with each factor being evaluated by a neural node that is part of a neural net and represented by a circle in FIG. 10. These factors may include at circle 1006 whether an initial contraction has occurred, at circle 1008 what is the slope of the sEMG signal 262 curve at the onset of the muscle cramp, at circle 1010 whether the first peak of muscle cramping has occurred as indicated by the sEMG signal 262, at circle 1012, the number of peaks that have occurred, and at circle 1014 the slope from a peak to the end of an event (e.g. when an sEMG signal 262 declines to reach close to a level that indicates regular muscular activity without any increase in activity within a predetermined timeframe). At circle 1027, it is determined whether the muscle contraction has ended. If so, then the process proceeds as described below.

At block 1016, it is determined whether the starting slope of the sEMG signal 262 is larger than the ending slope of the signal 262. At block 1018, it is determined whether a number of peaks in the sEMG signal 262 corresponds with a number of peaks in a typical contraction as represented by a comparison model stored in the models database 280, and at block 1020, it is determined whether a number of peaks in an event represented by sEMG data via an sEMG signal 262 is similar to the comparison model.

At circle 1022, it is determined whether a shape of the sEMG signal 262 fits the comparison model. If not, at block 1024, the model is adjusted according to the data represented by the sEMG signal 262. If the shape does fit the comparison model, then a determination is made as to the percent of the waveform that is within the model so that at block 1026, it is determined whether the shape of the sEMG waveform is within a predetermined acceptable range. If not, the process returns to block 1002 to receive additional raw data. At block 1027, it is determined whether a muscle cramping event is over. If the muscle cramping event is over, then at block 1028, the raw data is converted into waveform attributes as described in more detail below and added at block 1030 to a database of waveform attributes with a timestamp. The database of waveform attributes may be part of the database 280 or a separate database stored on the memory 219 or in another memory accessible by the application 218.

At block 1032, it is determined whether to provide an indication to a user or the treatment control unit directly to adjust the TENS treatment frequency. This determination may be based on a variety of considerations including trends of magnitude of the sEMG signal 262 indicating cramping at circle 1034, trends over time 1036, acceptable ranges 1038, acceptable amount of peaks 1040, treatment effectiveness 1042 and compensation for missing data 1044. Determinations at block 1046 of whether the current frequency of TENS treatment is helping and at block 1048 of whether a trend of muscle cramping in response to the treatment is moving up or down are also taken into account to determine whether to adjust the frequency of the TENS treatment at block 1050. Data from block 1032 may be used to adjust the comparison model at block 1051. The adjusted comparison model may then be provided as an output of the AI 248 back to circle 1022 as comparison model feedback. Data from circle 1040, scanning for a number of peaks, is fed back to block 1018 as input to determine whether there was an acceptable number of peaks. Similarly, data from circle 1038, scan for ranges, is provided to block 1026 to determine whether the shape of the waveform of the sEMG signal 262 was within an acceptable range that aligns with an actual contraction. This feedback and comparison are part of the machine learning of this embodiment.

As an additional input, at block 1052, user input may be received to indicate, for example, pain level, treatment effectiveness, etc. and affect downstream treatment options feeding back into the database of information at block 1030. Using the above-described approach, treatment effectiveness may be improved.

Figure 11:
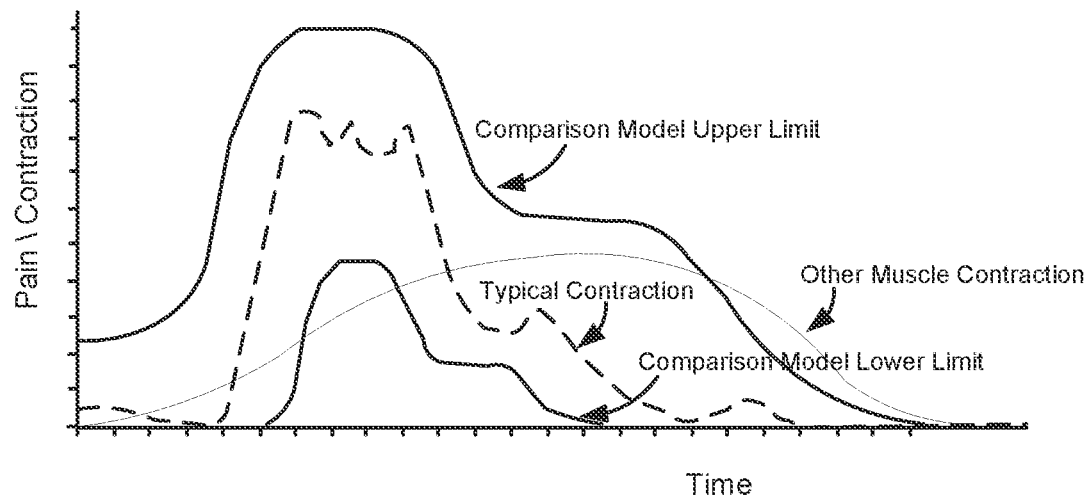
FIG. 11 illustrates an example initial comparison model that may be used in the process of FIG. 10.
Figure 12:
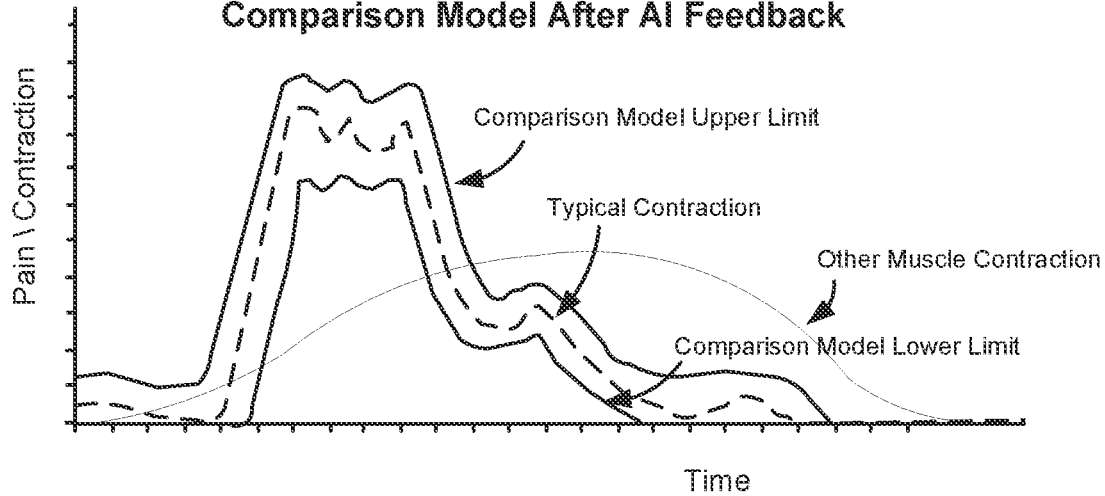
FIG. 12 illustrates an example model after a feedback process such as the process described in reference to FIG. 10.

FIG. 11 illustrates an example initial comparison model that may be used as an initial input to the AI 248 in a process such as the process described in reference to FIG. 10, while FIG. 12 shows an example of a model after a feedback process such as the process described in reference to FIG. 10 for embodiments related to the treatment of menstrual cramps.

Figure 13:
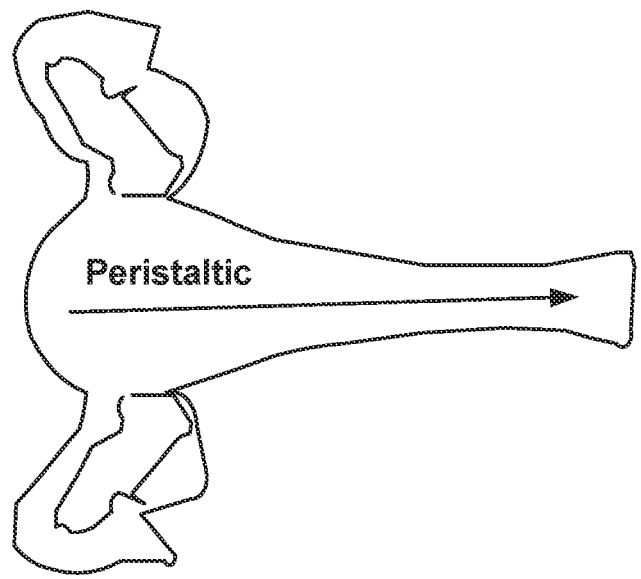
FIG. 13 illustrates an example of muscle cramping action for menstrual cramps that may be affected and/or measured by embodiments of the invention.

FIG. 13 illustrates an example of muscle cramping action for menstrual cramps that may be affected and/or measured by some embodiments over time.

Figure 14:
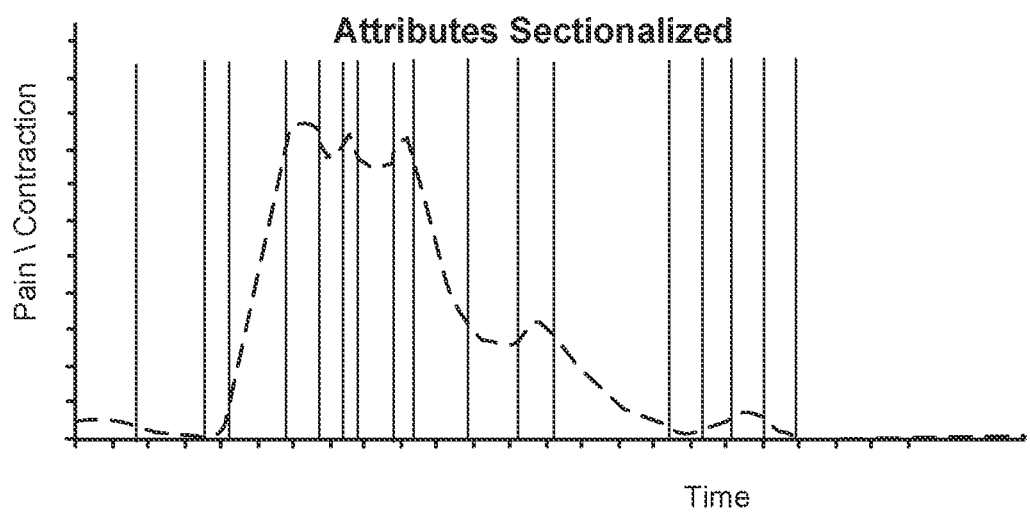
FIG. 14 illustrates an example of how attributes may be sectionalized to reduce the size of data sets of FIG. 10 according to some embodiments.

FIG. 14 illustrates how attributes of a waveform representing a muscle contraction (i.e. sEMG data) may be sectionalized for some embodiments to reduce the size of data sets that may be provided as inputs and/or outputs to/from the application 218 and/or the AI 248 as referred to at FIG. 10, block 1028, where raw data is converted into waveform attributes. For some embodiments, this process may be performed by a data reducer 252 (FIG. 2). The data reducer 252 may be implemented in software as instructions that are stored in a memory such as the memor(ies) 222 and executable by the controller 202. Alternatively, the data reducer 252 may be implemented using hardware or a combination of both hardware and software.

The X axis of FIG. 14 represents elapsed time. The sEMG data (i.e. the converted or filtered sEMG signal 262) is sampled, for example, every 0.1 sec for this type of real-time application. Sampling too frequently may provide more information than necessary while not sampling frequently enough may increase the possibility of error. The Y axis of FIG. 14 represents a magnitude of a muscle contraction as indicated by the sEMG data, which may correlate with a level of discomfort or pain. The pain/contraction measurement for some embodiments has the resolution of analog to digital converters (ADCs) in the controller 202 (FIG. 2) that receive the surface electromyography (sEMG) signal 262.

Each section of a waveform can be described as a curve with a starting point, an ending point, and a radius center point for the curve. A straight line can be described as a curve with an infinite radius. The starting point has an X and Y coordinate. The same is true for the ending point and the radius center point for the curve. The X coordinate value is a time stamp that may comprise 5 to 7 bytes of data for some embodiments. Y is defined by the ADC which can be described as 8 to 16 bits or 1 to 2 bytes. The radius center point is theoretical and can be a very large number as indicated by the focal point of the curve. Both the X and Y values for some embodiments allocate the most significant bit to indicate a positive or negative value. If all of the bits are 1 except for the positive/negative bit, the segment is considered a straight line.

One segment can be described with 21 bytes of data for some embodiments. Typically, an ADC reading may occur thousands of times during a segment depending on the segment. If it is assumed that there are 1000 double bytes of data, there are 2000 bytes of data that the data reducer 252 consolidates into a 21 data byte description. Each data segment may have the following structure: Starting Timestamp, Starting Pain Magnitude, Ending Timestamp, Ending Pain Magnitude, Radius Center Timestamp, Radius Center Pain Magnitude.

When a new segment starts, the first point has no radius. When the second point enters the equation, the radius is infinite because it is treated as a line. As each subsequent point is entered, the radius will move in towards the curve. Once the length of the radius stabilizes, the ending of the curve is determined by the radius moving away from the curve. The threshold of the changes will determine the ending point of the curve. Other approaches, including different data segment structures and numbers of bytes may be used for other embodiments.

Figure 15:
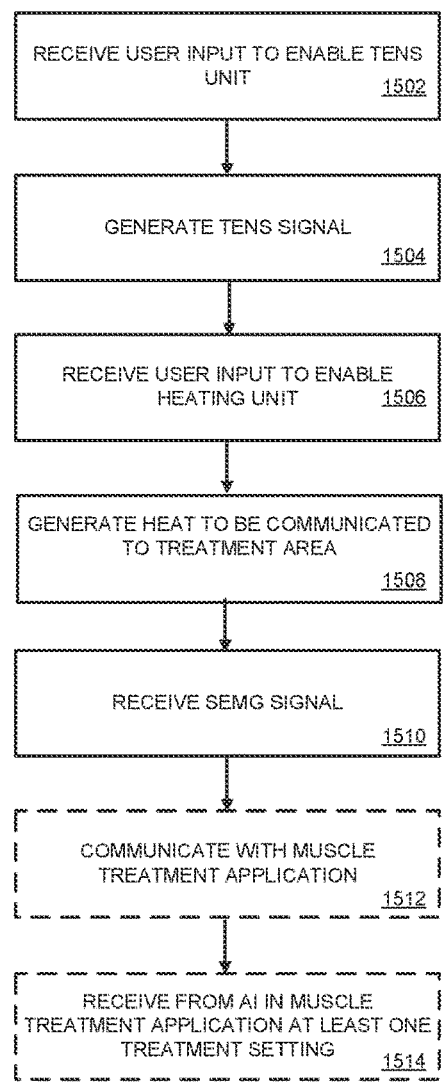
FIG. 15 is a flow diagram illustrating a method for treating muscular discomfort according to some embodiments.

FIG. 15 illustrates a process for treating muscular discomfort according to some embodiments. Some of the operations (or other processes described herein, or variations, and/or combinations thereof) are performed under the control of one or more computing devices or systems configured with executable instructions and are implemented as code (e.g. executable instructions, one or more computer programs, or one or more applications) executing collectively on one or more processors, by hardware or combinations thereof. The code is stored on a computer-readable storage medium, for example, in the form of a computer program comprising instructions executable by one or more processors. The computer-readable storage medium is non-transitory. In some embodiments, one or more of the operations are performed by the treatment pad 101 and/or the treatment control unit 102.

At block 1502, user input is received to selectively enable a TENS unit. At block 1504, a TENS signal to be communicated to a muscular area to be treated is generated based at least in part on the user input.

At block 1506, user input is received to selectively enable a heating unit and at block 1508, heat is generated and communicated to the muscular area to be treated based at least in part on the user input. At block 1510, a surface electromyography (sEMG) signal to indicate muscle activity in the muscular area to be treated is received.

For some embodiments, at block 1512, the process further includes communicating with a muscle treatment application on a remote device. This communication may include receiving user inputs regarding settings, providing treatment data, communicating with community users or other interactions. For embodiments for which the muscle treatment application 218 comprises at least one muscle treatment learning module such as an artificial intelligence (AI) module, at block 1514, the process further includes receiving from the muscle treatment application 218 a setting for at least one of the TENS signal frequency, the TENS signal intensity or the intensity of the heat, the setting being based at least in part on at least one of the received sEMG signal associated with the setting or user input indicating an effectiveness of the setting.

In the preceding description, various embodiments are described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

References to "one embodiment," "an embodiment," "an example embodiment," etc., indicate that the embodiment described may include a particular feature, structure, or characteristic, but every embodiment may not necessarily include the particular feature, structure, or characteristic.

Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Moreover, in the various embodiments described above, unless specifically noted otherwise, disjunctive language such as the phrase "at least one of A, B, or C" is intended to be understood to mean either A, B, or C, or any combination thereof (e.g., A, B, and/or C). As such, disjunctive language is not intended to, nor should it be understood to, imply that a given embodiment requires at least one of A, at least one of B, or at least one of C to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B, and C" can include a first processor configured to carry out recitation A working in conjunction with a second processor configured to carry out recitations B and C.

In embodiments, the term "engine" or "module" or "logic" may refer to, be part of, or include an application specific integrated circuit (ASIC), an electronic circuit, a processor (shared, dedicated, or group), and/or memory (shared, dedicated, or group) that execute one or more software or firmware programs, a combinatorial logic circuit, and/or other suitable components that provide the described functionality. In embodiments, an engine or a module may be implemented in firmware, hardware, software, or any combination of firmware, hardware, and software.

Embodiments of the invention may include various steps, which have been described above. The steps may be embodied in machine-executable instructions, which may be used to cause a general-purpose or special-purpose processor to perform the steps. Alternatively, these steps may be performed by specific hardware components that contain hardwired logic for performing the steps, or by any combination of programmed computer components and custom hardware components. Further, while the flow diagrams in the figures show a particular order of operations being performed by certain embodiments, it should be understood that such order is exemplary (e.g., alternative embodiments may perform the operations in a different order, combine certain operations, overlap certain operations, etc.).

As described herein, instructions may refer to specific configurations of hardware configured to perform certain operations or having a predetermined functionality or software instructions stored in memory embodied in a non-transitory computer machine-readable medium. Thus, the techniques shown in the figures can be implemented using code and data stored and executed on one or more electronic devices (e.g., an end station, a network element, etc.). Such electronic devices store and communicate (internally and/or with other electronic devices over a network) code and data using computer machine-readable media, such as non-transitory computer machine-readable storage media (e.g., magnetic disks; optical disks; random access memory; read only memory; flash memory devices; phase-change memory) and transitory computer machine-readable communication media (e.g., electrical, optical, acoustical or other form of propagated signals such as carrier waves, infrared signals, digital signals, etc.).

In addition, such electronic devices typically include a set of one or more processors coupled to one or more other components, such as one or more storage devices (non-transitory machine-readable storage media), user input/output devices (e.g., a keyboard, a touchscreen, and/or a display), and network connections. The coupling of the set of processors and other components is typically through one or more busses or bridges (also termed as bus controllers). The storage device and signals carrying the network traffic respectively represent one or more machine-readable storage media and machine-readable communication media. Thus, the storage device of a given electronic device typically stores code and/or data for execution on the set of one or more processors of that electronic device. Of course, one or more parts of an embodiment of the invention may be implemented using different combinations of software, firmware and/or hardware.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

What is claimed is:

1. An apparatus comprising:
   a treatment pad configured to be placed proximate to skin proximate to a muscular area to be treated, the treatment pad including at least a heating element comprising resistive heating fabric;
   a transcutaneous electrical nerve stimulation (TENS) unit coupled to the treatment pad;
   a surface electromyography (sEMG) unit coupled to the treatment pad; and
   a controller coupled to the TENS unit, the heating element and the sEMG unit, the controller configured to selectively control at least one of a frequency or an intensity of a TENS signal to be generated by the TENS unit to be applied to the muscular area to be treated, or an intensity of heat generated by the heating element, the controller further configured to receive an sEMG signal from the sEMG unit indicating muscle activity in the muscular area to be treated, wherein the controller further comprises a wireless unit configured to communicate with a remote device having access to a muscle treatment application comprising a muscle treatment learning module, the remote device comprising a processor, the muscle treatment application, when executed by the processor, configured to receive muscle treatment data from the controller, the muscle treatment data to include at least sEMG data associated with the received sEMG signal, the muscle treatment learning module configured to determine whether the received muscular treatment data indicates a muscular contraction.

2. The apparatus of claim 1 wherein the controller comprises a wireless unit configured to communicate with a remote device to access a muscle treatment application associated with the apparatus.

3. The apparatus of claim 2 wherein the remote device includes a processor, and wherein the muscle treatment application includes instructions that, when executed by the processor, identify a setting for at least one of the TENS signal frequency, the TENS signal intensity or the intensity of heat produced by the heating element.

4. The apparatus of claim 3 wherein the muscle treatment application, when executed by the processor, is configured to identify the setting based at least in part on stored muscle treatment data.

5. The apparatus of claim 4 wherein the muscle treatment data includes the setting for at least one of the TENS signal frequency, the TENS signal intensity, or the intensity of heat, and at least one of associated sEMG data from the sEMG signal or associated user feedback indicating an effectiveness of the setting.

6. The apparatus of claim 1 wherein the resistive heating fabric comprises a plurality of sections, the controller capable of powering one or more sections at a time.

7. The apparatus of claim 1 wherein each of the TENS unit and the sEMG unit comprise at least two electrodes configured to communicate respective signals between the muscular area to be treated and the respective unit.

8. The apparatus of claim 1 wherein the controller is disposed within a treatment control unit comprising a user interface configured to receive user input indicating at least one of a TENS signal frequency, TENS signal intensity or intensity of heat to be applied to the muscular area to be treated.

9. A computer-implemented method comprising:
  receiving, at a user interface of a treatment control unit, a first user input to selectively enable a transcutaneous electrical nerve stimulation (TENS) unit that is coupled to a treatment pad;
  generating, by the treatment control unit, a TENS signal to be communicated to a muscular area to be treated based at least in part on the user input, the TENS signal having a frequency and an intensity;
  receiving, at the user interface of the treatment control unit, a second user input to selectively enable a resistive heating element of the treatment pad comprising resistive heating fabric to generate heat having an intensity;
  receiving, by the treatment control unit, a surface electromyography (sEMG) signal at sEMG electrodes coupled to the treatment pad to indicate muscle activity in the muscular area to be treated;
  communicating with a remote device having access to a muscle treatment application comprising a muscle treatment learning module; and
  receiving an indication from the muscle treatment application, based on the sEMG signal, that the muscle activity is a muscular contraction.

10. The method of claim 9 further comprising communicating, by the treatment control unit, with a muscle treatment application on a remote device.

11. The method of claim 10 further comprising receiving from the muscle treatment application a setting for at least one of the frequency of the TENS signal, the intensity of the TENS signal or the intensity of the heat, the setting being based at least in part on at least one of the received sEMG signal or user input indicating an effectiveness of the setting.

12. The method of claim 9 further comprising storing, by the treatment control unit, treatment data indicating an effectiveness of a setting for one or more of a TENS frequency, a TENS intensity and a heat intensity.

13. The method of claim 12 further comprising, communicating, by the treatment control unit, via a network, the effectiveness of the setting to a community of users.

14. The method of claim 9 further comprising reducing, by the treatment control unit, data associated with the received sEMG signal.

15. An apparatus comprising:
  a treatment pad configured to be placed proximate to skin proximate to a muscular area to be treated;
  a transcutaneous electrical nerve stimulation (TENS) unit coupled to the treatment pad;
  a surface electromyography (sEMG) unit coupled to the treatment pad;
  a heating element comprising resistive heating fabric disposed within the treatment pad, the heating element comprising a plurality of sections, each section between two rails; and
  a controller coupled to the TENS unit, the sEMG unit, and the heating element, the controller capable of powering one or more sections of the heating element at a time by selectively coupling selected rails to one of a power source or a ground source, the controller further configured to selectively control at least one of a frequency or an intensity of a TENS signal to be generated by the TENS unit or an intensity of heat to be produced by the heating element, the controller further configured to receive an sEMG signal from the sEMG unit indicating muscle activity in the muscular area to be treated, wherein the controller further comprises a wireless unit configured to communicate with a remote device having access to a muscle treatment application, the remote device comprising a processor, the muscle treatment application, when executed by the processor, including a user interface configured to receive user input indicating at least one of a TENS signal frequency, TENS signal intensity or intensity of heat to be applied to the muscular area to be treated and wherein the muscle treatment application comprises at least a muscle treatment learning module, the muscle treatment learning module, when executed by the processor, configured to receive muscle treatment data from the controller, the muscle treatment data to include at least sEMG data associated with the received sEMG signal, the muscle treatment learning module configured to determine whether the received muscular treatment data indicates a muscular contraction.

16. The apparatus of claim 15 wherein the controller is disposed within a treatment control unit comprising a user interface configured to receive user input indicating at least one of a TENS signal frequency, TENS signal intensity or intensity of heat to be applied to the muscular area to be treated.

17. The apparatus of claim 15 wherein the muscle treatment application, when executed by the processor, is configured to identify a setting for at least one of the TENS signal frequency, the TENS signal intensity or the intensity of heat based at least in part on one of stored muscle treatment data associated with the setting and user feedback associated with the setting.

18. The apparatus of claim 15 wherein the wireless unit is further configured to communicate via a network to transmit muscle treatment data from the controller to a community of users, the muscle treatment data including at least sEMG data associated with the received sEMG signal, an associated frequency of the TENS signal, an associated intensity of the TENS signal and an associated intensity of the heat.

* * * * *